United States Patent [19]
Kupper et al.

[11] 3,968,180
[45] July 6, 1976

[54] PROCESS FOR THE PRODUCTION OF PURE CYCLOPENTENE

[75] Inventors: Friedrich-Wilhelm Kupper; Roland Streck, both of Marl, Germany

[73] Assignee: Chemische Werke Huls Aktiengesellchaft, Marl, Germany

[22] Filed: Oct. 22, 1974

[21] Appl. No.: 517,022

Related U.S. Application Data

[63] Continuation-in-part of Ser. No. 465,515, April 30, 1974.

[30] Foreign Application Priority Data

Dec. 21, 1973  Germany............................ 2363705

[52] U.S. Cl............................................. 260/666 A
[51] Int. Cl.².......................................... C07C 3/26
[58] Field of Search................................ 260/666 A

[56] References Cited
UNITED STATES PATENTS

| | | | |
|---|---|---|---|
| 3,558,518 | 1/1971 | Zuech.................................. | 252/429 |
| 3,634,539 | 1/1972 | Alkema et al. ................. | 260/683 D |
| 3,793,381 | 2/1974 | Kohler.............................. | 260/666 A |
| 3,816,384 | 6/1974 | Streck................................ | 260/666 A |

*Primary Examiner*—Delbert E. Gantz
*Assistant Examiner*—C. E. Spresser
*Attorney, Agent, or Firm*—Millen, Raptes & White

[57]  ABSTRACT

A process for the production of cyclopentene free of $C_5$-diene impurities, which comprises metathetically reacting cis,cis-cyclodecadiene-(1,6) with a catalytic amount of a metathesis catalyst comprising a support material and an oxide of an element of Group VI A or VII A of the Periodic Table, at a reaction temperature of from 0°C up to the temperature at which said catalyst decomposes, for a period of time sufficient to form said cyclopentene.

8 Claims, No Drawings

PROCESS FOR THE PRODUCTION OF PURE CYCLOPENTENE

CROSS-REFERENCE TO RELATED APPLICATION

This application is a continuation-in-part of copending, commonly assigned U.S. Patent Application Ser. No. 465,515 filed April 30, 1974, the contents of which are incorporated by reference herein.

BACKGROUND OF THE INVENTION

This invention relates to a process for the production of pure cyclopentene.

It is known to obtain cyclopentene from diolefin-containing hydrocarbon mixtures, e.g., pyrolysis benzines or cracked gasoline containing cyclopentene, cyclopentadiene and/or dicyclopentadiene by selectively hydrogenating the diolefins in the hydrocarbon mixture to monoolefins and isolating the cyclopentene by distillative separation, e.g., see German Unexamined Laid-Open Application DOS 1,643,947, Furthermore, it is known from DOS 1,793,254 to obtain cyclopentene, together with isoprene and a diolefin stream containing essentially 1,3-pentadiene and cyclopentadiene, from $C_5$-hydrocarbon mixtures by subjecting the hydrocarbon mixture to a liquid-liquid extraction with 1-oxo-1-methyl-phospholine as the selective solvent, in combination with an extractive distillation. DOS 1,793,256 likewise describes a process for the separation of $C_5$-hydrocarbon mixtures and for obtaining polymerizable cyclopentene, using N-methyloxazolidone as the selective solvent.

It is furthermore known from DOS 1,793,273 to separate the selective solvent, after liquid-liquid extraction and extractive distillation, in a liquid-liquid counter extraction from the $C_5$-diolefins with a second solvent and to employ a portion of the $C_5$-hydrocarbon vapors at the head of the distillation column for separation of the second solvent from the diolefins to operate the extractive distillation stage.

DOS 2,025,411 describes the production of cyclopentene from cyclopentadiene by partial hydrogenation with molecular hydrogen in the gaseous phase at temperatures of above 50°C with a supported hydrogenation catalyst containing palladium as the active component with additives of chromium and/or titanium.

Finally, it is known from DOS 2,131,791 to treat cyclopentene containing olefinic and diolefinic $C_5$-hydrocarbon impurities with an acidic cation exchanger and thereafter to separate cyclopentene from the thus-obtained product by means of distillation.

All of the above-described processes in the present state of the art presuppose the isolation of cyclopentadiene-cyclopentene mixtures from $C_5$-cuts, which are commercially available only in limited amounts so that quantitative production of cyclopentene is limited. A further disadvantage of such processes is that economical isolation of the cyclopentene is possible only in conjunction with simultaneous exploitation of the isoprene component of the $C_5$-cut. A usable quality of cyclopentene is obtained only by way of several stages, some of which are technologically complicated. Furthermore, since a complete lack of diene in the cyclopentene, desirable for a polymerization of the cyclopentene with the aid of so-called metathesis catalysts, is not ensured in the prior art processes, there is often an increased consumption of catalyst during polymerization. This, in turn, leads to either more expensive working-up processes or to an increased ash content in the polymers.

U.S. Patent Application Ser. No. 465,515 describes a process for the preparation of pure cyclopentene wherein cis, cis-1,6-cyclodecadiene is reacted with a metathesis catalyst, optionally in the presence of a solvent, at temperatures of above 0°C.

In a further development of this process, it has now been found that pure cyclopentene can be produced by employing a heterogeneous metathesis catalyst comprising a. a support material and
b. an oxide of the elements of Group VI A or VII A of the Mendeléyev Periodic Table of the elements.

OBJECTS OF THE INVENTION

Accordingly, it is a general object of the present invention to provide a process for the production of pure cyclopentene which minimizes or eliminates the above-mentioned problems facing the current state of the art.

Another object of the present invention is to provide a new method for the direct preparation of pure cyclopentene.

A further object of the present invention is to provide a process for the production of pure cyclopentene which does not employ the conventional $C_5$-hydrocarbon mixtures as a starting material.

An additional object of the present invention is to provide a method for the production of cyclopentene free from contamination with $C_5$-dienes.

Yet another object of the present invention is to eliminate the hydrogenation step heretofore employed in the preparation of cyclopentene.

Other objects and advantages of this invention will become apparent to those skilled in the art upon further study of the specification and appended claims.

SUMMARY OF THE INVENTION

Briefly, the above and other objects are attained in one aspect of the present invention by providing a process for the production of cyclopentene free of $C_5$-diene impurities which comprises metathetically reacting cis, cis-cyclodecadiene-(1,6) with a catalytic amount of a metathesis catalyst comprising one or more oxides of at least one element of Group VI A or VII A of the periodic table on a solid support, at a reaction temperature of from 0°C up to the temperature at which said catalyst decomposes, for a period of time sufficient to form said cyclopentene.

DETAILED DISCUSSION

It has now been found that pure cyclopentene can be produced in an elegantly simple manner by metathetically reacting cis,cis-cyclodecadiene-(1,6), optionally in the presence of an inert solvent, at temperatures of above 0°C. with a supported olefin metathesis catalyst containing an oxide of an element of Group VI A or VII A of the periodic table.

The pure cyclopentene produced according to the present invention is a product which inherently does not contain any conjugated dienes which can be confirmed by ultraviolet spectroscopy, e.g., cyclopentadiene, and such a product is especially valuable for subsequent polymerization with the aid of metathesis catalysts.

The starting material employed in the process of this invention, cis,cis-cyclodecadiene-(1,6), can be produced in accordance with known processes. For example, cis,trans-cyclodecadiene-(1,5) can first be produced from the inexpensive monomers butadiene and ethylene, which are available in almost unlimited amounts, e.g., see G. Wilke and P. Heimbach, "Angew. Chemie" (Applied Chemistry)75: 10 (1963). This cis,-trans-cyclodecadiene-(1,5) can then be converted to cis,cis-cyclodecadiene-(1,6) with the aid of an isomerizing catalyst, e.g., see German Pat. No. 1,230,023 or dissertation by H. G. Nuessel, Ruhr University Bochum (1970), p. 89.

As is known, metathesis catalysts are understood in the art to mean homogeneous and heterogeneous catalysts containing compounds of metals of Subgroups V to VII of the Periodic Table, predominantly compounds of niobium, tantalum, molybdenum, tungsten and rhenium, as well as optionally compounds of the metals of main Groups I to III of the Periodic Table, e.g. the alkyls or hydrides thereof, optionally with further ligands, e.g. halogen, alkoxyl or carboxylate or, in place thereof, Lewis acids. The metathesis catalysts, as is known, can further contain activating additives, e.g. alcohols, expoxides, tert.-butyl hypochlorite, peroxides, carboxylic acids, aromatic nitro compounds, vinyl halides, vinyl and allyl ethers, vinyl and allyl esters, etc.

The heterogeneous metathesis catalysts used in accordance with this invention comprise (a) a support material and (b) at least one oxide of one or more elements of Group VI A or VII A of the periodic table of the elements.

Suitable support materials are well known in the art and include but are not limited to those commercially available aluminum oxides or oxides of the elements of Group IV of the periodic table of the elements which are solid under the contemplated reaction conditions, preferably silicon dioxides. These difficult-to-melt oxides ordinarily contain a minor proportion, e.g. 0.01–1.5%, preferably 0.1–1.0%, of alkali metal ions stemming from the manufacturing process, e.g. in the case of aluminum oxide, about 0.4% by weight of $Na_2O$ is suitable.

Preferably, oxides of molybdenum and rhenium are used as the catalyst component (b); rhenium heptoxide is particularly preferred.

The heterogeneous catalysts can be prepared conventionally, e.g. by simply mixing the components together. However, a preferred process resides in impregnating the support material with the solution of a suitable oxide precursor compound of the above-mentioned transition metals and then activating the support. The term "activation" means a heat or other treatment whereby the compounds are converted into the corresponding oxides. Preferably, a catalyst is utilized in the present process wherein aluminum oxide is impregnated with a solution of a perrhenate, especially ammonium perrhenate and then heated in an air or oxygen stream so that the perrhenate is converted into rhenium oxide. The conversion of the compounds of the aforementioned transition metals into the oxides is generally accomplished by simple heating in a temperature range of 300°–650°C., preferably in the range of 350°–450°C.

The heterogeneous metathesis catalysts usable in the process of this invention generally contain 1–30 parts, preferably 5–20 parts of molybdenum oxide or rhenium oxide in the valence stage active during the metathesis reaction per 100 parts of support material.

In principle, all such metathesis catalysts suitable for the polymerization of cyclic olefins having at least one unsubstituted ring double bond are useful in the process of the art and include but are not limited to those meeting one or more of the following criteria:

a. those in which component a) is a particulate aluminum oxide or silicon dioxide;

b. those in which the metal of component b) is an oxide of molybdenum or rhenium;

c. those in which component b) is rhenium heptoxide;

d. those in which component a) is an aluminum oxide containing 0.1–1.0% alkali metal as $Na_2O$;

e. those in which component a) is particulate aluminum oxide having an average particle size mean diameter of 1 – 6 mm; a surface area of 250–350m²/g; a pore volume of 0.45–0.55cm³/g; a bulk density of 700–900g/l; and an alkali content of 0.02–1.0wt.%;

f. those of (a) thru (e) inclusive containing 1–30 parts, preferably 5–20 parts by weight of active metal oxide per 100 parts of support material.

The process of this invention can be effected discontinuously as well as continuously. Suitably, the course of the reaction is chosen so that the thus-formed cyclopentene is separated as soon as possible from the reaction zone. The product can then optionally be subjected to a distillative purification. The cis,cis-1,6-cyclodecadiene is brought into contact with the catalyst until it is completely consumed.

The varying boiling points of cis,cis-1,6-cyclodecadiene and cyclopentene make it possible to withdraw the latter in an optimum manner by suitable selection of the pressure in the reaction apparatus.

The reaction can optionally also be accomplished in an inert solvent, i.e. one which does not interfere with metathetical reactions employing the aforementioned catalysts. Suitable inert solvents are well known in the art and are generally characterized as aliphatic, alicyclic, aromatic and/or halogenated hydrocarbons. Suitable such solvents include but are not limited to aliphatic hydrocarbons, e.g., pentane, hexane, heptane, n- and iso-octane, isononane (hydrogenated propene trimer), n-dedane, isododecane, (hydrogenated propene tetramer); cycloaliphatic hydrocarbons, e.g., cyclopentane, cyclohexane and the substitution products thereof, e.g., methylcyclopentane, methylcyclohexane, ethylcyclohexane, isopropylcyclohexane, cyclooctane, decahydronaphthalene, etc; hydrogenated terpenes, e.g. pinane and camphane; aromatic hydrocarbons, e.g., benzene, toluene, o-, m-, p-xylene, ethylbenzene, o-, m-, p-diethylbenzene, n-propylbenzene, isopropylbenzene, other mono- to polyalkyl benzenes, tetrahydronaphthalene, etc; and halogenated derivatives of the above, e.g., methylene chloride, chloroform, carbon tetrachloride, 1,2-dichloroethylene, trichloroethylene, tetrachloroethylene, chlorobenzene, o-dichlorobenzene, trichlorobenzene (mixture of isomers), bromobenzene, fluorobenzene, 1,2-dichloroethane, etc.

Preferably, solvents are employed which cannot participate as reactants in a Friedel-Crafts reaction with olefins present, i.e. the starting material or the cyclopentene product, so as to avoid Friedel-Crafts side reactions.

It is essential that the inert solvents as well as the cis,cis-cyclodecadiene-(1,6) be made maximally free of water and other proton donors, as well as of compounds having electron donor functions (Lewis bases), by means of a suitable known purification technique.

Except for very small quantities which are optionally used for obtaining special effects, such impurities generally impair the catalyst activity.

The process of the present invention is generally conducted at temperatures of above 0°C. The reaction temperature has an upper limit determined by the thermal stability of the catalyst and its support, and a lower limit determined by an excessive reduction of the reaction velocity. The process is advantageously carried out at temperatures of between 40° and 180°C, especially between 50° and 120°C. As with the choice of a support material, reaction temperatures will be chosen as that isomerization side reactions are extensively prohibited. Reaction times required are those typical of metathesis reactions and vary from several minutes to several days, generally 0.25–10 hours at the preferred temperatures.

After a satisfactory conversion has been attained, as determined, e.g. by gas chromatography, the catalyst is inactivated and/or separated, and the thus-produced cyclopentene is isolated by distillation. The unreacted cis,cis-cyclodecadiene-(1,6) can be recycled into the reaction process after having been worked up appropriately, e.g., by fractional distillation and/or recrystallization.

The cyclopentene product produced according to the process of the present invention is completely free of $C_5$-diolefins so long as there are no diolefin contaminants in either the cis,cis-cyclodecadiene-(1,6) starting material or the solvent employed except, of course, for unreacted starting material which is readily separated from the cyclopentene product, e.g., by simple distillation. As both the starting material and solvent are readily obtainable or easily purified to be free of diolefin contaminants and as none are inherently produced in the course of the reaction, unreacted starting material can be readily recycled. Thus, the process can be conducted batchwise, discontinuously or continuously resulting in substantial savings in both materials and steps employed. Furthermore, since usable yields are obtained under mild reaction conditions in relatively brief reaction times, the process itself is particularly economical. Thus, it will generally but not always be advantageous to terminate the reaction after a yield of 10 - 15% has been reacted, based on conversion of the starting material, although higher yields, e.g., of 20 – 30% or even higher, can be obtained if desired.

The cyclopentene produced according to the process of this invention is excellently suited for use in the production of trans-1,5-polypentenamer rubber which is of great technical interest, e.g., see Hydrocarbon Processing, December 1972, p. 71. The preparation of cyclopentene according to the present process is surprising insofar as cis,cis-cyclodecadiene-(1,6) cannot be converted into unsaturated high molecular weight products by means of the metathesis catalysts described herein within the temperature range which is utilized for the preparation of polyalkenamers from other cycloolefins, and would thus appear to be unsuitable for the metathesis reaction.

While not wishing to be bound by an theory of the invention, it is believed that the metathesis reaction of the present invention takes place as follows:

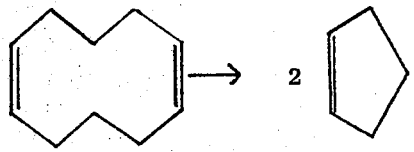

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight.

EXAMPLES 1–10 cis,cis-1,6-Cyclodecadiene is charged into a three-necked flask equipped with an internal thermometer and capillary under an inert gas atmosphere. The flask is provided with a circulation apparatus comprising a riser, a Liebig condenser, a Soxhlet-type thermostat-equipped extractor, and a graduated dropping funnel with pressure compensation disposed underneath the extractor. The extractor serves for receiving the heterogeneous metathesis catalyst, while the dropping funnel is intended for controlling the amount of cis,cis-1,6-cyclodecadiene passing the catalyst, which can flow back from the dropping funnel into the three-necked flask. The thus-formed cyclopentene is withdrawn by means of a vacuum nipple mounted above the extractor and is condensed in a cooling trap.

The extractor contains 38 g. of a catalyst prepared in the following way: 88 g. of an aluminum oxide (surface: 300 m²/g., pore volume: 0.5 cm3/g., bulk density: 880 g./l., alkali content: 0.4% by weight $Na_2O$) is impregnated with a solution of 11 g. of ammonium perrhenate in 100 ml. of distilled water; excess water is withdrawn via the rotary evaporator, the remaining residue is dried under vacuum at 100°–120°C. and then heated for 5–20 hours in a tubular furnace at 380°–420°C.

The following table contains the results obtained when varying the process parameters:

| Example No. | Variable | Reaction Temp. °C. | Pressure (mm.) | Duration of Experiment (min.) | Cyclopentene Obtained (g.) | 1,6-CDD Throughput per Hour (ml./h.) | Cyclopentene / Total Throughput 1,6-CDD (mg./ml.) |
|---|---|---|---|---|---|---|---|
| 1 | Temperature | 60 | 146 | 424 | 2.7 | 531 | 0.71 |
| 2 | " | 100 | 147 | 432 | 9.7 | 549 | 2.45 |
| 3 | " | 60 | 146 | 412 | 6.0 | 180 | 5.14 |
| 4 | " | 100 | 150 | 424 | 14.6 | 184 | 11.20 |
| 5 | Residence Time | 60 | 100 | 433 | 5.3 | 570 | 1.28 |
| 6 | " | 60 | 100 | 427 | 5.8 | 174 | 4.68 |
| 7 | " | 60 | 100 | 121 | 8.2 | 103 | 39.42 |
| 8 | " | 100 | 148 | 432 | 9.7 | 549 | 2.45 |
| 9 | " | 100 | 146 | 426 | 8.2 | 387 | 2.98 |

-continued

| Example No. | Variable | Reaction Temp. °C. | Pressure (mm.) | Duration of Experiment (min.) | Cyclopentene Obtained (g.) | 1,6-CDD Throughput per Hour (ml./h.) | Cyclopentene / Total Throughput 1,6-CDD (mg./ml.) |
| --- | --- | --- | --- | --- | --- | --- | --- |
| 10 | " | 100 | 146 | 416 | 8.4 | 1.89 | 6.41 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

By the term "free of $C_5$-diene impurities" as used herein is meant a $C_5$-diene content of less than 0.1 wt. %, preferably less than 0.05 wt. % based on the total reaction mixture.

What is claimed is:

1. In a process for the production of cyclopentene free of $C_5$-diene impurities, which comprises metathetically reacting cis,cis-cyclodecadiene-(1,6) with a catalytic amount of a metathesis catalyst capable of promoting the ring-opening polymerization of cyclic olefin having at least one unsubstituted ring double bond at a metathesis reaction temperature of from 0°C. up to the temperature at which said catalyst decomposes for a period of time sufficient to form said cyclopentene having a $C_5$-diene content of less than 0.1 weight percent of the total reaction mixture, the improvement which comprises employing a heterogeneous metathesis catalyst consisting essentially of
   a. a solid catalyst support material, and
   b. an oxide of molybdenum or of rhenium.

2. A process according to claim 1, wherein the reaction temperature is 40°–180° C.

3. A process according to claim 2, wherein the reaction temperature is 50°–120°C.

4. A process according to claim 1, wherein the solid support material is an aluminum oxide containing 0.1–1% by weight alkali metal ions as $Na_2O$.

5. In a process for the production of cyclopentene free of $C_5$-diene impurities, which comprises metathetically reacting cis,cis-cyclodecadiene-(1,6) with a catalytic amount of a metathesis catalyst capable of promoting the ring-opening polymerization of cyclic olefin having at least one unsubstituted ring double bond at a metathesis reaction temperature of from 0°C. up to the temperaure at which said catalyst decomposes for a period of time sufficient to form a reaction product consisting essentially of said cyclopentene having a $C_5$-diene content of less than 0.1 weight percent of the total reaction mixture, the improvement which comprises employing a heterogeneous metathesis catalyst consisting essentially of
   a. a solid catalyst support material;
   b. an oxide of molybdenum or of rhenium; and
   c. a catalyst activator selected from the group consisting of alcohols, epoxides, tert.-butyl hypochlorite, peroxides, carboxylic acids, aromatic nitro compounds, vinyl halides, vinyl and allyl ethers and vinyl and allyl esters.

6. A process according to claim 4, wherein component
   a. is particulate aluminum oxide having an average particle size mean diameter of 1–6 mm; a surface area of 250–350m²/g; a pore volume of 0.45–0.55cm³/g; a bulk density of 700–900g/l; 1; and an alkali content of 0.02–1.0wt.%

7. A process according to claim 4, wherein component b) is rhenium heptoxide.

8. A process according to claim 1, wherein the reaction is effected in an inert diluent which cannot participate in a Friedel Crafts reaction with olefins present.

* * * * *

UNITED STATES PATENT OFFICE
CERTIFICATE OF CORRECTION

PATENT NO. : 3,968,180
DATED : JULY 6, 1976
INVENTOR(S) : Friedrich-Wilhelm Kupper et al It is certified that error appears in the above-identified patent and that said Letters Patent are hereby corrected as shown below:

[73] Assignee: Should be -- Chemische Werke Huels Aktiengesellschaft --.

Signed and Sealed this

Twenty-third Day of November 1976

[SEAL]

Attest:

RUTH C. MASON
Attesting Officer

C. MARSHALL DANN
Commissioner of Patents and Trademarks